United States Patent

Jakobsen et al.

Patent Number: 5,102,894
Date of Patent: Apr. 7, 1992

[54] SUBSTITUTED PIPERIDINE COMPOUNDS AND THEIR USE

[75] Inventors: Palle Jakobsen, Vaerløse; Ursula Sonnewald, Trondheim, both of Denmark

[73] Assignee: Novo Nordisk A/S, Bagsvaerd, Denmark

[21] Appl. No.: 623,868

[22] Filed: Dec. 3, 1990

[30] Foreign Application Priority Data

Dec. 18, 1989 [DK] Denmark .............................. 6402/89

[51] Int. Cl.$^5$ .................. A61K 31/445; C07D 405/04; C07D 407/04; C07D 409/04
[52] U.S. Cl. .................................... 514/319; 514/321; 514/326; 546/197; 546/206; 546/208; 546/213
[58] Field of Search ............... 546/197, 206, 208, 213, 546/214; 514/326, 319, 321

[56] References Cited

U.S. PATENT DOCUMENTS

| | | | |
|---|---|---|---|
| 2,895,965 | 7/1959 | Eugster et al. | 546/214 X |
| 4,877,799 | 10/1989 | Drejer et al. | 514/317 |
| 4,985,446 | 1/1991 | Drejer et al. | 514/321 |
| 5,017,585 | 5/1991 | Jakobsen et al. | 514/317 |
| 5,019,582 | 5/1991 | Drejer et al. | 514/321 |

Primary Examiner—Richard L. Raymond
Attorney, Agent, or Firm—Steve T. Zelson; Elias J. Lambiris

[57] ABSTRACT

Novel piperidine compounds having the formula I

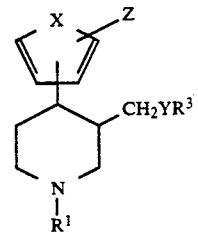

wherein $R^3$ is 3,4-methylenedioxyphenyl, phenyl, naphthyl, which are optionally substituted with one or two halogen, amino, $C_{1-6}$-alkyl mono-or disubstituted amino group, $C_{1-6}$-alkoxy, cyano, mono-, di- or trihalogenated $C_{1-6}$-alkyl, $C_{2-6}$-alkenyl, $C_{1-6}$alkyl, $C_{3-5}$-alkylene, trifluoromethoxy, or trifluoromethyl groups, $R^1$ is hydrogen, straight or branched $C_{1-8}$-alkyl, $C_{1-8}$-alkoxy-$C_{1-8}$-alkyl, $C_{3-8}$-cycloalkyl, $C_{2-6}$-alkenyl, $C_{4-8}$-cycloalkylalkyl, $C_{2-6}$-alkynyl Z is hydrogen, straight or branched $C_{1-8}$-alkyl, Y is O or S X is O, S or NR, wherein R is hydrogen or $C_{1-4}$-alkyl or a salt thereof with a pharmaceutically acceptable acid.

The novel compounds are useful in the treatment of anoxia, traumatic injury, ischemia, migraine and epilepsy.

6 Claims, No Drawings

SUBSTITUTED PIPERIDINE COMPOUNDS AND THEIR USE

The present invention relates to therapeutically active piperidine compounds, a method of preparing the same and to pharmaceutical compositions comprising the compounds. The novel compounds are useful in the treatment of anoxia, traumatic injury, ischemia, migraine and epilepsy.

It is well known that accumulation of calcium in the brain cells (calcium overload) is seen after periods of uncontrolled hyperactivity in the brain, such as after convulsions, migraine, anoxia and ischemia. As the concentration of calcium in the cells is of vital importance for the regulation of cell function, an uncontrolled high concentration of the cell calcium will lead to, or indirectly cause the symptoms and possibly also the degenerative changes combined with the above diseases.

Therefore, calcium overload blockers selective for brain cells will be useful in the treatment of anoxia, traumatic injury, ischemia, migraine and epilepsy.

Well known calcium antagonists such as nifedipine, verapamil and diltiazem have activity against peripheral calcium uptake, e.g. in blood vessels and the heart, however, they have shown only very low activity against calcium overload in brain cells.

Accordingly it is an object of the invention to provide novel compounds having activity against calcium overload in brain cells.

The novel compounds of the invention are piperidine compounds having the general formula I

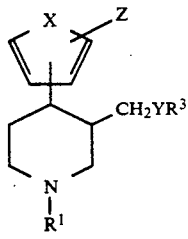

I wherein
$R^3$ is 3,4-methylenedioxyphenyl, phenyl, naphthyl, which are optionally substituted with one or two halogen, amino, $C_{1-6}$-alkyl mono-or disubstituted amino group, $C_{1-6}$-alkoxy, cyano, mono-, di- or trihalogenated $C_{1-6}$- alkyl, $C_{2-6}$-alkenyl, $C_{1-6}$-alkyl, $C_{3-5}$-alkylene trifluoromethoxy, or trifluoromethyl groups,
$R^1$ is hydrogen, straight or branched $C_{1-8}$-alkoxy-$C_{3-8}$-cycloalkyl, $C_{1-8}$-alkoxy-$C_{1-8}$-alkyl, $C_{3-8}$-cycloalkyl, $C_{2-6}$-alkenyl, $C_{4-8}$-cycloalkylalkyl, $C_{2-6}$-alkynyl
Z is hydrogen, straight or branched $C_{1-8}$-alkyl,
Y is O or S
X is O, S or NR, wherein R is hydrogen or $C_{1-4}$-alkyl
and a salt thereof with a pharmaceutically acceptable acid.

Examples of such salts include inorganic and organic acid addtion salts such as hydrochloride, hydrobromide, sulphate, phosphate, acetate, fumarate, maleate, citrate, lactate, tartrate, oxalate, or similar pharmaceutically-acceptable inorganic or organic acid addition salts.

The invention also relates to methods of preparing the above mentioned compounds. These methods comprises a) reacting a compound having the formula II

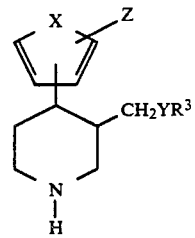

II wherein X, Y, Z, R and $R^3$ have the meanings defined above, with a compound having the general formula $R^1$-V, wherein V is a leaving group such as halogen or sulfonates and $R^1$ has the meaning defined above, or b) reacting a compound having the formula III

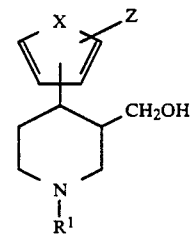

III wherein X, Z and $R^1$ have the meanings defined above with an organic or inorganic acid chloride, giving a compound of formula IV

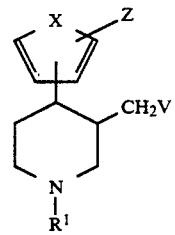

IV wherein V is a leaving group as defined above and reacting a compound of formula IV with a compound having the general formula $R^3YH$ wherein Y and $R^3$ have the meanings defined above, to form a compound of formula I, or c) reacting a compound having the formula III

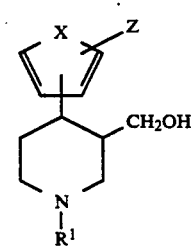

III wherein X, Z and $R^1$ have the meanings defined above, with a compound having the formula V

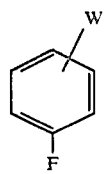

wherein W is trifluoromethyl or nitro by means of strong base (e.g. NaH or alkoxide), to form a compound of formula I, wherein Y is O, and $R^3$ is phenyl substituted with trifluoromethyl or nitro.

The pharmacological properties of the compounds of the invention can be illustrated by determining their capability to inhibit calcium uptake into brain synaptosomes.

PRINCIPLE

Depolarization of neuronal membranes leads to an opening of socalled 'voltage operated calcium channels' (VOC) in the membranes which allows a massive influx of calcium from the extracellular space. A crude synaptosomal preparation (socalled $P_2$ fraction) contains small vesicles surrounded by neuronal membrane and it is possible in such a preparation to study a depolarization-induced opening of VOC. In the present model $^{45}$Ca influx is induced in the synaptosomes by depolarization with elevated potassium concentrations, and the effect of test substances on this stimulated uptake is studies (Nachshen, D. A. and Blaustein, M. P., Mol. Pharmcol., 16, 579 (1979)).

ASSAY

A male Wistar rat is decapitated and the cerebral cortex removed and homogenized in 10 ml of ice-cold 0.32 M sucrose using a glass homogenizer with a teflon pestle. All subsequent steps for isolation of synaptosomes are done at 0°-4° C. The homogenate is centrifuged at 1000×g for 10 min and the resulting supernatant is re-centrifuged at 18000×g for 20 min. This pellet ($P_2$) is resuspended in 0.32 M sucrose (5 ml per g of original tissue) with a teflon pestle.

Aliquots (0.050 ml) of this crude synaptosomal suspension are added to glass tubes containing 0.625 ml of NaCl buffer (136 mM NaCl, 4 mM KCl 0.35 mM $CaCl_2$, 1.2 mM $MgCl_2$, 20 mM Tris HCl, 12 mM glucose, pH 7.4) and 0.025 ml of various drug solutions in 48% Ethanol. The tubes are pre- incubated for 30 min on ice and then for 6 min at 37° C. in a water bath.

The uptake is immediately initiated by adding 0.4 ml of $^{45}CaCl_2$ (specific activity=29-39 Ci/g; 0.5 Ci/assay), in 145 mM NaCl for non-depolarized samples and in 145 mM KCl for depolarized samples. The incubation is continued for 15 s.

The uptake is terminated by rapid filtration through GF-C glass fiber filters which are washed three times with 5 ml of a cold solution containing 145 mM KCl, 7 mM EGTA and 20 mM Tris HCl, pH 7.4. The amount of radioactivity on the filter disc is determined by liquid scintillation spectrometry.

TEST PROCEDURE

Test substances are dissolved in 10 ml of 48% ethanol at a concentration of 0.44 mg/ml. Dilutions are made in 48% ethanol to give final concentrations of 0.1, 0.3, 1, 3 and 10 μg/ml. Experiments are performed in triplicate. Controls for depolarized and nondepolarized samples are included in the assay and test substances are only tested in depolarized samples. 25-75% inhibition of stimulated uptake must be obtained before calculating the $IC_{50}$ value.

RESULTS

The test value will be given as $IC_{50}$ (the concentration (μg/ml), of test substance which inhibit 50% of stimulated uptake of $^{45}$Ca (uptake in depolarized samples)). The $IC_{50}$ value is estimated from dose response curves. Test results obtained by testing some compounds of the present invention will appear from the following table 1

TABLE 1

| Compound | $IC_{50}$ (μg/ml) |
| --- | --- |
| Compound 3 | 5.3 |
| Compound 12 | 18 |
| Compound 15 | 7.2 |
| Compound 25 | 9.1 |
| Compound 27 | 13 |
| Compound 28 | 30 |
| Compound 31 | 4.7 |
| Compound 30 | 4.9 |
| Compound 37 | 3.6 |
| Compound 39 | 2.7 |
| Compound 43 | 10 |
| Compound 47 | 5.8 |
| Compound 48 | 12 |
| Compound 44 | 2.8 |
| *Nifedipine | 26 |
| *Verapamil | 16 |
| *Diltiazem | >90 |
| *Flunarizine | 20 |

*well known calcium antagonists

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets of filled capsules, or liquids, such as solutions, suspensions, emulsions, elixirs, or capsules filled with the same, all for oral use, in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective calcium overload blocking amount of the active ingredient commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elizir of the like can be used in cases where a sweetened vehicle can be employed.

Generally, the compounds of this invention are dispensed in unit form comprising 0.05-100 mg in a pharmaceutically acceptable carrier per unit dosage.

The dosage of the compounds according to this invention is 0.1-300 mg/day, preferably 10-100 mg/day, when administered to patients, e.g. humans, as a drug.

A typical tablet which may be prepared by conventional tabletting techniques contains:

| Active compound | 5.0 mg |
|---|---|
| Lactosum | 67.8 mg Ph.Eur. |
| Avicel TM | 31.4 mg |
| Amberlite TM IRP 88 | 1.0 mg |
| Magnesii stearas | 0.25 mg Ph.Eur. |

Due to the high calcium overload blocking activity, the compounds of the invention are extremely useful in the treatment symptoms related to an accumulation of calcium in brain cells of mammals, when administered in an amount effective for blocking activity of compounds of the invention includes both activity against anoxia, traumatics injury, ischemia, migraine and epilepsy. The compounds of the invention may accordingly be administered to a subject, e.g., a living animal body, including a human, in need of a calcium overload blocker, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective calcium overload blocking amount, and in any event an amount which is effective for the treatment of anoxia, traumatic injury, ischemia, migraine, epilepsy, or neurodegenerative diseases due to their calcium overload blocking activity. Suitable dosage ranges are 1-200 milligrams daily, 10-100 milligrams daily, and especially 30-70 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples.

EXAMPLE 1 trans
1-methyl-4-(2-thienyl)-3-(3-trifluorommethylphenoxymethyl) piperidine, HCl (1)

3-hydroxymethyl-1-methyl-4-(2-thienyl) piperidine (9.5 g) was dissolved in dry toluene (300 ml), triethylamine (12.5 ml) and benzenesulphonyl chloride (7 ml) were added and the reaction mixture stirred at R.T. for 5 h. Water was added and the toluene phase separated, dried with $MgSO_4$ and evaporated to dryness. The resulting oil was purified by $OH^-/CH_2Cl_2$ extraction resulting in an oil (10.3 g) identified as 3-benzenesulphonyloxymethyl-1-methyl-4-(2- thienyl) piperidine (2) by $^1H$ NMR.

Compound (2) (4.8 g) was dissolved in MIBC (125 ml) and added to a solution of NaOH (0.5 g) and 3-trifluoromethylphenol (1.8 ml) in MIBC (100 ml). Reflux for 2 h. extracted with $H_2O$. The MIBC layer was evaporated and extracted with $OH^-$/ether. The combined ether layers were evaporated to dryness, and the resulting mass purified on silicagel using $CH_3OH/CH_2Cl_2$ (1/9) as eluent gave (1) (1.1 g) which was precipitated as the hydrochloride from acetone/ether. M.p. 158.4° C.

trans 1-methyl-3-(3,4-methylenedioxyphenoxymethyl)-4(2- thienyl) piperidine, HCl (4) was prepared from (2) and 3,4-methylenedioxyphenol as described for compound (1). Precipitated as the hydrochloride. M.p. 226.3° C.

trans 3-(3,4-methylenedioxyphenoxymethyl)-1-pentyl-4-(3- thienyl) piperidine, oxalate (5) was prepared from 3-hydroxymethyl-1-pentyl-4-(3-thienyl) piperidine and sesamol using the procedure described for the preparation of (1). Precipitated as the oxalate from acetone. M.p. 94° C.

EXAMPLE 2

4-(2-thienyl)-3-(3-trifluoromethylphenoxymethyl) piperidine, oxalate (6)

Compound (1) (0.8 g as dry base) was dissolved in dry toluene, 1-chloroethyl chloroformate (0.43 ml) was dropwise added and the mixture refluxed for 4 h. The mixture was subsequently evaporated to almost dryness, $CH_3OH$ was added and the reflux continued for 2h. Evaporation to dryness followed by purification on silicagel column using $CH_2Cl_2/CH_3OH$ (9/1) as eluent gave (6) (0.4 g) precipitated from ether/acetone as the oxalate. M.p. 150° C.

3-(3,4-methylenedioxyphenoxymethyl)-4(2-thienyl) piperidine, oxalate (7) was prepared from (4) using the method described for the preparation of (6), precipitated as the oxalate. M.p. 249.4° C.

EXAMPLE 3 trans
1-pentyl-4-(2-thienyl)-3-(3-trifluoromethylphenoxymethyl) piperidine, oxalate (8)

(6) (0.3 g), 1-bromopentane (1.3 ml) and $K_2CO_3$ (1 g) were refluxed in abs. ethanol (25 ml) for 4 h. After addition of acetone/ether the mixture was filtered, and evaporated to dryness. The residue was extracted with $OH^-$/ether and the etheral layer dried and evaporated. The resulting oil was dissolved in acetone and precipitated with anhydrous oxalic acid giving (8) (0.12 g). M.p. 120.8° C.

(+ −)trans 1-pentyl-4-(2-thienyl)-3-(3-trifluoromethylphenoxymethyl)piperidine, HCl (33) was prepared from the basic form of (8) by precipitation with HCl in acetone-ether solution. M.p. 138.8°–139.8° C.

trans 3-(3,4-methylenedioxyphenoxymethyl)-1-pentyl-4-(2-thienyl) piperidine, oxalate (9) was prepared from (7) and pentylbromide as described for (8). Isolated from acetone/ether as the oxalate. M.p. 128.7° C.

EXAMPLE 4 trans 1-butyl-4-(5-methyl-2-furyl)-3-(3,4-methylenedioxyphenoxymethyl) piperidine, HCl (10)

1-butyl-3-hydroxymethyl-4-(5-methyl-2-furyl) piperidine (6.7 g) was dissolved in toluene (100 ml). Triethylamine (7 ml) and benzenesulphonyl chloride (3.8ml) were added and the mixture stirred overnight at R.T. and subsequently 1 h. at reflux temperature. Rinse up as described in example 1 gave 9.9 g of 3-benzenesulphonyloxymethyl-1l-butyl- 4-(5-methyl-2-furyl)-piperidune (11)) identified by $^1$H NMR.

Compound (11) (4.9 g) was dissolved in MIBC (75 ml) and added to a solution of sesamol (1.75 g) and NaOH (0.55 g) in MIBC (50 ml). Reflux 5 h. Rinse up as described in example 1 gave (10) (0.5 g). M.p. 146°–147° C.

trans 1-butyl-4-(5-methyl-2-furyl)-3-(3-trifluoromethylphenoxyethyl) piperidine, HCl (12) was prepared from (11) as described for compound (10) using 3-trifluoromethylphenol. M.p. 152.5°–153.5° C.

EXAMPLE 5 trans 1-butyl-4-(1-methyl-2-pyrrolyl)-3-(4-trifluoromethylphenoxymethyl) piperidine, oxalate (13)

1-butyl-3-hydroxymethyl-4-(1-methyl-2-pyrrolyl) piperidine (2.2 g) was dissolved in dry DMF. NaH (1 eq) was added and the mixture refluxed for 1.5 h. Subsequently 4-fluoro-trifluoromethylbenzene (1.75 g) was added and the mixture refluxed overnight. Evaporation to dryness followed by extraction with H2O/ether, isolation of the etheral layer, evaporation to dryness and purification on a silica gel column with ethyl acetate as eluent gave (13) precipitated as the oxalate. M.p. 123°–125° C.

EXAMPLE 6

3-benzenesulphonyloxymethyl-1-pentyl-4-(2-thienyl)-piperidine (14) was prepared from 3-hydroxymethyl-1-pentyl-4-(2-thienyl)piperidine (13 g), benzenesulphonyl chloride (13 ml) and triethylamine (12.5 ml) in dry toluene (100 ml) as described for (2). Yield: 20.4 g, mass spectrum (M+ 407) in accordance with proposed structure The following compounds were prepared from (14) and the appropriate substituted phenol using the same method as described for the preparation of (1).

(+ −) trans 3-(2-cyanophenoxymethyl)-1-pentyl-4-(2-thienyl)piperidine, HCl (15) From 2-cyanophenol (0.85 g) and (14) (2.5 g). Yield: 0.5 g (15). M.p. 216°–219° C.

(+ −) trans 3-(3-cyanophenoxymethyl)-1-pentyl-4-(2-thienyl)piperidine, HCl (16) From 3-cyanophenol (0.85 g) and (14) (2.5 g). Yield: 0.6 g (16). M.p. 74.3° C.

(+ −) trans 3-(4-cyanophenoxymethyl-1-pentyl-4-(2-thienyl)piperidine, HCl (17) From 4-cyanophenol (0.85 g) and (14) (2.5 g). Yield: 0.4 g (17). M.p. 73.2° C.

(+ −) trans 3-(3-methoxyphenoxymethyl)-1-pentyl-4-(2-thienyl)piperidine, HCl (26) From 3-methoxy (0.6 g) and (14) (1.5 g). NaH was used in stead of NaOH as base and DMF as solvent. Heating at 100° C. for 1 h. Yield of (26): 0.75 g. M.p. 78°–80° C.

EXAMPLE 7

(+ −) trans 1-pentyl-4-(2-thienyl)-3-(4-trifluoromethylphenoxymethYl)piperidine, oxalate (18)

3-hydroxymethyl-1-pentyl-4-(2-thienyl)piperidine (2 g) was dissolved in dimethylacetamide (15 ml). NaH (0.5 g) was added and the mixture warmed to 70° C. for 0.5 h. p-Fluorobenzotrifluoride (1 ml) was added and the mixture refluxed for 10 h. Subsequently the mixture was poured into water and extracted with ether. The etheral layer was dried, evaporated to dryness and the resulting product precipitated as the oxalate. Yield of (18): 1.4 g. M.p. 87°–88° C.

(+ −) trans 1-(2-methylbutyl)-4-(3-thienyl)-3-(4-trifluoromethylphenoxymethyl)piperidine, HCl (19) was prepared as described for (18) from 3-hydroxymethyl-1-(2-methylbutyl)-4-(3-thienyl)piperidune (2 g). Reflux time 3 h. Yield: 1.4 g of (19) precipitated as the hydrochloride. M.p. 160° C.

(+ −) trans 1-pentyl-4-(3-thienyl)-3-(4-trifluoromethylphenoxymethyl)piperidine, HCl (20) Preparation from 3-hydroxymethyl-1-pentyl-4-(3-thienyl)piperidine (0.7 g) and p-fluorobenzotrifluoride (0.38 ml) as described for (18), reflux 3 h. Yield: 0.22 g. M.p. 131°–133° C.

(+ −) trans 1-butyl-4-(2-thienyl)-3-(2-trifluoromethylphenoxymethyl)piperidine, HCl (21) Preparation from 1-butyl-3-hydroxymethyl-4-(2-thienyl)piperidine (1 g) and o-fluorobenzotrifluoride (0.5 ml) as described for (18). Reflux for 20 h. Yield: 0.85 g, of a hard glass.

EXAMPLE 8

3-benzenesulphonyloxymethyl-1-butyl-4-(2-thienyl)-piperidine (22) was prepared as described for (14) from 1-butyl-3-hydroxymethyl-4-(2-thienyl)piperidine (10 g). Yield: 10 g of (22), the mass spectrum showed a degradation pattern in accordance with the proposed structure (M+ 393).

The following compounds were prepared from (22) and the appropriate substituted phenol, using the method described for the preparation of (1).

(+ −) trans 1-butyl-4-(2-thienyl)-3-(3-trifluoromethoxyphenoxymethyl)piperidine, HCl (23) From 2-trifluoromethoxyphenol (1.3 g) and (22) (2.5 g), reflux 8 h. Yield: 0.45 g (23). M.p. 130°–132° C.

(+ −) trans 1-butyl-4-(2-thienyl)-3-4-trifluoromethoxyphenoxymethyl)piperidine, HCl (24) From (22) (2.5 g) and 4-trifluoromethoxyphenol (1.3 g), heating for 10 h. Yield of (24): 0.55 g. M.p. 155°–156° C.

(+ −) trans 1-butyl-4-(2-thienyl)-3-(3-methoxyphenoxymethyl)piperidine, HCl (25) From (22) (2.1 g) and 3-methoxyphenol (1.0 g), heating at 100° C. for 8 h. Yield of (25): 0.6 g. M.p. 148°–149° C.

(+ −) trans 1-butyl-3-(2-isopropoxyphenoxymethyl)-4-(2-thienyl)piperidine, oxalate (27) From (22) (2.1 g) and 2-isopropyloxyphenol (1.2 g), heating at 110° C. for 6 h. Yield: 1.0 g. M.p. 89°–90° C.

EXAMPLE 9

(+ —) trans 3-(3-aminomethylphenoxymethyl)-1-pentyl-4-(2-thienyl)piperidine, HCl (28) (16) 0.42 g was dissolved in dry THF (25 ml) and reduced by means of LiAlH$_4$ (0.18 g in 25 ml THF) and 50° C. for 5 h. Rinse up by OH$^-$/ether extraction followed by precipitation with HCl gave (28) 0.15 g. M.p. 127°–128° C.

EXAMPLE 10

3-benzenesulphonyloxymethyl-1-pentyl-4-(3-thienyl)piperidine (29) Prepared from 3-hydroxymethyl-1-pentyl-4-(3-thienyl)piperidine (4 g) and benzenesulphonyl chloride (2 ml) in dry toluene (50 ml) as described for (2). Yield: 4.7 g, identified from its $^1$H NMR spectrum.

The following compounds were prepared from (29) and the appropriately substituted phenol, using the method described for the preparation of (1) using NaH as the base and DMF as solvent:

(+ —) trans 3 -(3,4-methylenedioxyphenoxymethyl)-1-pentyl-4-(3-thienyl)piperidine, HCl (30) From sesamol (0.55 g) and (29) (1.5 g), heating at 80° C. for 2 h. Yield: 0.9 g. M.p. 112°–115° C.

(+ —) trans 1-pentyl-4-(3-thienyl)-3-(3-trifluoromethylphenoxymethyl)piperidine, oxalate (31) From 5 g (29) and 1.5 ml 3-trifluoromethyl phenol, heating at 85° C. for 3 h. Yield: 3.2 g. M.p. 117°–118° C.

(+ —) trans 3-(4-methoxyphenoxymethyl)-1-pentyl-4-(3-thienyl)piperidine, HCl (32) From p-methoxyphenol (0.5) g) and (29) 1.5 g, heating at 80° C. for 2 h. Yield: 0.77 g. M.p. 100°–102° C.

(+ —) trans 3-(4-fluorophenoxymethyl)-1-pentyl-4-(3-thienyl)piperidine, HCl (33) From 0.56 g 4-fluorophenol and 2 g (29), heating at 85° C. for 10 h. Yield: 0.7 g. M.p. 141° C.

(+ —) trans 3-(3,4-dichlorophenoxymethyl)-1-pentyl-4-(3-thienyl)piperidine, HCl (34) From 3,4-dichlorophenol (0.9 g) and (29) (2 g), heating at 80° C. for 4 h. Yield: 0.7 g. M.p. 133.5° C.

(+ —) trans 1-pentyl-3-(5,6,7,8-tetrahydro-2-naphthoxymethyl)-4-(3-thienyl)piperidine, HCl (35) From 5,6,7,8-tetrahydro-2-naphthol (0.8 g) and (29) (2 g), heating at 80° C. for 4 h. Yield: 1.1 g. M.p. 175°–176° C.

(+ —) trans 3-(3-methylphenoxymethyl)-1-pentyl-4-(3-thienyl)piperidine, HCl (36) From m-cresol (0.7 g) and (29) (2 g), heating at 80° C. for 4 h. Yield: 0.87 g. M.p. 117°–118° C.

(+ —) trans 3-(4-chlorophenoxymethyl)-1-pentyl-4-(3-thienyl)piperidine, HCl (37) From p-chlorophenol (0.6 g) and (29) (2 g), heating at 80° C. for 8 h. Yield: 0.9 g. M.p. 117° C.

(+ —) trans 3-(3-cyanophenoxymethyl)-1-pentyl-4-(3-thienyl)piperidine, HCl (38) From 2.3 g (29) and 3-cyanophenol (0.75 g), heating at 100° C. for 3 h. Yield. 2 g of a hard glass, identified by $^1$H-NMR.

(+ —) trans 3-(4-cyanophenoxymethyl)-1-pentyl-4-(3-thienyl)piperidine, HCl (39) From 4-cyanophenol (0.75 g) and (29) (2.3 g) by heating at 100° C. for 3 h. Yield: 1.2 g. M.p. 110° C.

(+ —) trans 3-(3-nitrophenoxymethyl)-1-pentyl-4-(3-thienyl)piperidine, HCl (40) From 3-nitrophenol 0.85 g) and (29) (2.0 g), heating at 100° C. for 3 h. Yield: 1 g. M.p. 121° C.

(+ —) trans 3-(4-nitrophenoxymethyl)-1-pentyl-4-(3-thienyl)piperidine, HCl (41) From 4-nitrophenol (0.85 g) and (29) (2.0 g), heating at 100° C. for 2 h. Yield: 1.0 g. M.p. 177°–78° C. (+ —) trans 3-(3-methoxyphenoxymethyl)-1-pentyl-4-(3-thienyl)piperidine, HCl (42) From 3-methoxyphenol (0.7 g) and (29) (2 g), heating at 90° C. for 2 h. Yield: 1.3 g. M.p. 148° C.

(+ —) trans 3-(4-trifluoromethoxyphenoxymethyl)-1-pentyl-4-(3-thienyl)piperidine, HCl (43) From 4-trifluoromethoxyphenol (1.0 g) and (29) (2 g) by heating at 90° C. for 2 h. Yield: 1.0 g. M.p. 132° C.

EXAMPLE 11

(+ —) trans 4-(thienyl)-3-(3-trifluoromethylphenoxymethyl)piperidine, HCl (44) was prepared from (31) on its basic form (3.2 g) and 1-chloroethyl chloroformate (1 ml) in 1,2-dichloroethane (50 ml).

The chloroformate was added dropwise to the solution of (31) at 0° C. and subsequently the mixture was heated to 70° C. for 2 h. After standing at RT overnight the solvent was evaporated and the residue refluxed in 50 ml MeOH for 2h. Rinse up on silicagel column with CH$_2$Cl$_2$/CH$_3$OH 9/1 as eluent. Yield: 1.25 g. M.p. 140°–141° C.

EXAMPLE 12

3-benzenesulphonyloxymethyl-1-(2-methylbutyl)-4-(3-thienyl)piperidine (45) Preparation from 3-hydroxymethyl-1-(2-methylbutyl)-4-(3-thienyl)piperidine, (14 g) and benzenesulphonyl chloride (6.7 ml) in dry toluene (100 ml) as described for (2). Yield: 17 g, identified by its $^1$H NMR spectrum.

(+ —) trans 1-(2-methylbutyl)-3-(3,4-methylenedioxyphenoxymethyl)-4-(3-thienyl)piperidine, HCl (46) was prepared from sesamol (0.55 g) dissolved in dry DMF. NaH (0.5 g) was added and the mixture heated to 70° C. for 0.5 h. Subsequently (45) (1.5 g) was added and the resulting mixture was heated at 80° C. for 2 h. The mixture was poured into water and extracted with ether. The etheral layer was evaporated and the resulting product purified on silicagel using ethyl acetate as eluent. Yield: 1.0 g. M.p. 186°–188° C.

(+ —) trans(2-methylbutyl)-4-(3-thienyl)-3-(3-trifluoromethylphenoxymethyl)piperidine, HCl (47) was prepared as described for (46) from 3-trifluoromethylphenol (0.65 g) and (45) (1.5 g) by heating to 80° C. for 2.5 h. Yield: 1.1 g. M.p. 149°–151° C.

(+ —) trans 3-(4-methoxyphenoxymethyl)-1-(2-methylbutyl)-4-(3-thienyl)piperidine, HCl (48) from p-methoxyphenol and 1.5 g (45) by heating at 80° C. as described for (46). Yield: 1.2 g. M.p. 129°–135° C.

(+ —) trans 3-(3-methoxyphenoxymethyl)-1-(2-methylbutyl)-4-(3-thienyl)piperidine, HCl (49) From 3-methoxyphenol (0.5 g) and (45) (1.5 g) by heating to 80° C. for 10 h as described for (46). Yield: 0.4 g. M.p. 150°–152° C.

(+ —) trans (2-methybutyl)-4-(3-thienyl)-3-(4-trifluoromethoxyphenoxymethyl)piperidine, HCl (50) From 4-trifluoromethoxyphenol (0.71 g) and (45) (1.5 g) by heating to 80° C. for 6 h following the procedure described for (46). Yield: 0.4 g. M.p. 167°–168° C.

EXAMPLE 13

(+ —) trans 1-cyclopropylmethyl-4-(3-thienyl)-3-(3-trifluoromethylphenoxymethyl)piperidine, HCl (51) Prepared from (44) (0.7 g) and bromomethyl cyclopropane (0.29 ml) in ethanol using the method described for (8). Yield: 56.5%. M.p. 140°–142° C. (+ —) trans 1-cyclopentyl-4-(3-thienyl)-3-(3-trifluoromethylphenoxymethyl)piperidine, HCl (52) From (44) (0.7 g) and cyclopentyl bromide (0.45 g) as described for the preparation of (8). Yield: 27.3%. M.p. 221.8° C. (+—) trans 1-(3-methylbutyl)-4-(3-thienyl)-3-(3-trifluoromethylphenoxymethyl)piperidine, HCl (52) From (44) (0.7 g) and 1-bromo-3-methylbutane (0.45 g) as described for the preparation of (8). Yield: 41.4%. M.p. 141.7° C.

We claim:

1. A compound of formula I

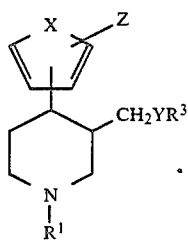

wherein

R[1] is hydrogen, straight or branched $C_{1-8}$-alkyl, $C_{1-8}$-alkoxy-$C_{1-8}$-alkyl, $C_{3-8}$-cycloalkyl, $C_{2-6}$-alkenyl, $C_{4-8}$-cycloalkylalkyl or $C_{2-6}$-alkynyl;

R[3] is 3,4-methylenedioxyphenyl, phenyl, naphthyl, each of which may be optionally substituted with one or two halogen, amino, $C_{1-6}$-alkyl mono- or disubstituted amino, $C_{1-6}$-alkoxy, cyano, mono-, di- or trihalogenated $C_{1-6}$-alkyl, $C_{2-6}$-alkenyl, $C_{1-6}$alkyl, $C_{3-5}$alkylene, trifluoromethoxy, or trifluoromethyl groups;

X is O, S or NR, wherein R is hydrogen or $C_{1-4}$-alkyl;

Y is O or S; and

Z is hydrogen or straight or branched $C_{1-8}$-alkyl; or a pharmaceutically acceptable salt thereof.

2. A compound according to claim 1 selected from the following:

trans 1-methyl-4-(2-thienyl)-3-(3-trifluoromethylphenoxymethyl) piperidine, trans 1-pentyl-4-(3-thienyl)-3-(3-trifluoromethylphenoxymethyl) piperidine, 4-(2-thienyl)-3-(3-trifluoromethylphenoxymethyl) piperidine, 1-pentyl-4-(2-thienyl)-3-(3-trifluoromethylphenoxymethyl) piperidine, trans 3-(3,4-methylenedioxyphenoxymethyl)-1-pentyl-4-(2-thienyl) piperidine, trans 1-butyl-4-(1-methyl-2-pyrrolyl)-3-(4-trifluoromethylphenoxymethyl) piperidine, trans 1-butyl-4-(5-methyl-2-furyl)-3-(3,4-methylenedioxyphenoxymethyl) piperidine, trans 1-butyl-4-(5-methyl-2-furyl)-3-(3-trifluoromethylphenoxymethyl) piperidine, (+—) trans (2-methylbutyl)-4-(3-thienyl)-3-(3-trifluoromethylphenoxymethyl)piperidine, (+—) trans 1-pentyl-4-(3-thienyl)-3-(4-trifluoromethylphenoxymethyl)piperidine, (+—) trans 3-(4-chlorophenoxymethyl)-1-pentyl-4-(3thienyl)piperidine, (+—) trans 3-(4-cyanophenoxymethyl)-1-pentyl-4-(3thienyl)piperidine, (+—) trans 4-(3-thienyl)-3-(3-trifluoromethylphenoxymethyl)piperidine, or a salt thereof with a pharmaceutically acceptable acid.

3. A pharmaceutical composition comprising an effective amount of a compound according to claim 1, together with a pharmaceutically-acceptable carrier or diluent.

4. A pharmaceutical composition according to claim 3 in the form of an oral dosage unit containing 1–100 mg of the active compound.

5. A method of treating an indication related to calcium overload in brain cells of mammals, including humans, in a subject in need thereof, comprising administering to said subject a compound according to claim 1.

6. A method of treating an indication related to calcium overload in brain cells of mammals, including humans, in a subject in need thereof, comprising administering to said subject a pharmaceutical composition according to claim 3.

* * * * *